(12) United States Patent
Sharma et al.

(10) Patent No.: US 12,616,502 B2
(45) Date of Patent: May 5, 2026

(54) INTRODUCER SHEATH WITH DUAL ARM HUB HAVING INBUILT TIGHTENING PORT

(71) Applicants: Boston Scientific Medical Device Limited, Galway (IE); Boston Scientific Scimed, Inc., Maple Grove, MN (US)

(72) Inventors: Neeraj Kumar Sharma, Delhi (IN); Qian Liu, Plymouth, MN (US); Boney Augustine, Bhopal (IN)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 84 days.

(21) Appl. No.: 18/659,441

(22) Filed: May 9, 2024

(65) Prior Publication Data

US 2024/0374287 A1     Nov. 14, 2024

Related U.S. Application Data

(60) Provisional application No. 63/465,958, filed on May 12, 2023.

(51) Int. Cl.
A61B 17/34          (2006.01)
A61M 25/06          (2006.01)

(52) U.S. Cl.
CPC ...... A61B 17/3498 (2013.01); A61B 17/3423 (2013.01); A61B 2017/3464 (2013.01);
(Continued)

(58) Field of Classification Search
CPC ............ A61B 17/3498; A61B 17/3423; A61B 2017/3464; A61B 2017/347;
(Continued)

(56) References Cited

U.S. PATENT DOCUMENTS

| | | |
|---|---|---|
| 5,254,097 A | 10/1993 | Schock et al. |
| 5,295,969 A | 3/1994 | Fischell et al. |

(Continued)

FOREIGN PATENT DOCUMENTS

| | | |
|---|---|---|
| EP | 1229948 B1 | 6/2005 |
| EP | 3866876 B1 | 11/2022 |

(Continued)

OTHER PUBLICATIONS

International Search Report and Written Opinion for International Application No. PCT/US2024/028529, dated Sep. 23, 2024. (17 Pages).

*Primary Examiner* — Richard G Louis
(74) *Attorney, Agent, or Firm* — Seager, Tufte & Wickhem LLP

(57) ABSTRACT

An introducer sheath including a valve hub and an elongate shaft extending from the valve hub. The valve hub defines a main port and a side port. The main port includes a hub body, a compressible seal disposed within the hub body, a pusher at least partially positioned within the hub body and slidably movable relative thereto, and a lock nut surrounding the pusher. The lock nut is threadably engaged with the hub body such that rotation of the lock nut moves the pusher axially toward and/or away from the compressible seal.

14 Claims, 8 Drawing Sheets

(52) U.S. Cl.
CPC .................. *A61B 2017/347* (2013.01); *A61M 2025/0681* (2013.01)

(58) Field of Classification Search
CPC .. A61M 2025/0681; A61M 2039/0258; A61M 2039/0633; A61M 2039/0673; A61M 25/0097; A61M 25/0662; A61M 2039/062; A61M 2039/0686; A61M 39/0613; A61M 39/06
See application file for complete search history.

(56)                    References Cited

U.S. PATENT DOCUMENTS

| | | | |
|---|---|---|---|
| 5,352,215 A * | 10/1994 | Thome ................. | A61M 39/10 604/533 |
| 5,935,112 A | 8/1999 | Stevens et al. | |
| 6,692,462 B2 | 2/2004 | Mackenzie et al. | |
| 7,027,875 B2 | 4/2006 | Siess et al. | |
| 8,888,728 B2 | 11/2014 | Aboul-Hosn et al. | |
| 9,937,319 B1 | 4/2018 | Leeflang et al. | |
| 10,709,828 B2 | 7/2020 | Toellner et al. | |
| 10,737,008 B2 | 8/2020 | Corbett et al. | |
| 11,833,314 B2 | 12/2023 | Corbett et al. | |
| 2001/0044600 A1 * | 11/2001 | Elkins ............... | A61M 16/0463 604/119 |
| 2003/0085373 A1 * | 5/2003 | Dehdashtian ..... | A61M 39/0606 251/149.3 |
| 2003/0088213 A1 | 5/2003 | Schweikert et al. | |
| 2005/0085789 A1 | 4/2005 | Khan et al. | |
| 2005/0197624 A1 | 9/2005 | Goodson et al. | |
| 2006/0047266 A1 | 3/2006 | Elkins et al. | |
| 2008/0033396 A1 | 2/2008 | Danek et al. | |
| 2008/0188831 A1 | 8/2008 | Bonnette et al. | |
| 2009/0259200 A1 | 10/2009 | Lampropoulos et al. | |
| 2010/0100044 A1 | 4/2010 | Ye et al. | |
| 2011/0004223 A1 * | 1/2011 | Leeflang ................ | B21D 28/32 606/108 |
| 2011/0077621 A1 | 3/2011 | Graham et al. | |
| 2014/0025037 A1 | 1/2014 | Elkins et al. | |
| 2015/0141738 A1 | 5/2015 | Toellner et al. | |
| 2017/0049947 A1 | 2/2017 | Corbett et al. | |
| 2018/0256875 A1 * | 9/2018 | Agrawal ............... | A61M 39/06 |
| 2019/0167967 A1 | 6/2019 | Mottola et al. | |
| 2020/0121905 A1 | 4/2020 | Zoll | |
| 2020/0289794 A1 | 9/2020 | Fantuzzi | |
| 2020/0391014 A1 | 12/2020 | Walters et al. | |
| 2021/0085923 A1 | 3/2021 | Fantuzzi et al. | |
| 2021/0361926 A1 | 11/2021 | Corbett et al. | |
| 2023/0270988 A1 | 8/2023 | Sharma et al. | |

FOREIGN PATENT DOCUMENTS

| | | |
|---|---|---|
| WO | 9813083 A1 | 4/1998 |
| WO | 2016001439 A1 | 1/2016 |
| WO | 2019032520 A2 | 2/2019 |
| WO | 2024177974 A1 | 8/2024 |

* cited by examiner

INTRODUCER SHEATH WITH DUAL ARM HUB HAVING INBUILT TIGHTENING PORT

CROSS REFERENCE TO RELATED APPLICATIONS

This application claims the benefit of U.S. Provisional Patent Application Ser. No. 63/465,958, filed May 12, 2023, which is incorporated herein by reference.

TECHNICAL FIELD

The present disclosure pertains to sheaths for delivering intravascular medical devices. More specifically, the present disclosure relates to a hub of a sheath with a tightening port for securing a medical device, such as a catheter or blood pump, within the hub and thus fix the position of the catheter with respect to the hub and sheath.

BACKGROUND

In various procedures for delivering intravascular medical devices, a sheath is inserted into a blood vessel of a patient, for example a femoral artery, and one or more medical devices may be advanced through the sheath and into the patient's vasculature. In various instances, the medical devices include catheters or other devices, such as a blood pump. A hub may be incorporated at a proximal end of the sheath to provide access to a lumen of an elongate shaft of the sheath. The hub may include one or more seals, e.g., hemostasis seals, to reduce blood leakage as devices are being inserted, positioned, and removed. In various instances, there may be a desire to fix the position of the medical device within the sheath and vasculature. Additionally, there may be a desire to reposition the medical device within the vasculature. Thus, there is a need for improved hub configurations for a sheath including sealing mechanisms to reduce blood leakage past the medical device and/or tightening mechanisms for securing the medical device, such as a catheter or blood pump, within the sheath and vasculature that also allow repositioning of the medical device in the vasculature.

BRIEF SUMMARY

This disclosure provides design, material, manufacturing method, and use alternatives for medical devices, including introducer and/or repositioning sheaths.

A first example is directed to an introducer sheath including a valve hub and an elongate shaft extending from the valve hub. The valve hub defines a main port and a side port. The main port includes a hub body, a compressible seal disposed within the hub body, a pusher at least partially positioned within the hub body and slidably movable relative thereto, and a lock nut surrounding the pusher. The lock nut is threadably engaged with the hub body such that rotation of the lock nut moves the pusher axially toward and/or away from the compressible seal.

Alternatively or additionally to any of the examples above, in another example, the pusher includes first and second tabs extending radially from a body of the pusher.

Alternatively or additionally to any of the examples above, in another example, the first and second tabs are positioned in first and second slots in the hub body, respectively.

Alternatively or additionally to any of the examples above, in another example, the first and second tabs extend in opposite directions.

Alternatively or additionally to any of the examples above, in another example, an internal rim of the lock nut engages the first and second tabs.

Alternatively or additionally to any of the examples above, in another example, the introducer sheath further includes a first O-ring surrounding a distal portion of the pusher and a second O-ring surrounding a proximal portion of the pusher.

Alternatively or additionally to any of the examples above, in another example, the first and second tabs are located between the first O-ring and the second O-ring.

Alternatively or additionally to any of the examples above, in another example, the pusher extends proximal of the hub body.

Alternatively or additionally to any of the examples above, in another example, the main port includes an elastomeric seal, wherein the pusher is positioned between the compressible seal and the elastomeric seal.

Alternatively or additionally to any of the examples above, in another example, the elastomeric seal includes one or more slits.

Alternatively or additionally to any of the examples above, in another example, the side port includes an elastomeric seal including one or more slits formed therein.

Another example is an introducer sheath. The introducer sheath includes a valve hub defining a main port and a side port, and an elongate shaft extending from the valve hub. The main port includes a hub body, a compressible seal disposed within the hub body, an elastomeric seal proximal of and spaced apart from the compressible seal, and a lock nut threadably engaged with the hub body such that rotation of the lock nut moves the compressible seal between an opening position and a closed position.

Alternatively or additionally to any of the examples above, in another example, the introducer sheath includes a pusher engaged with the lock nut, such that rotation of the lock nut causes the pusher to axially move toward and/or away from the compressible seal.

Alternatively or additionally to any of the examples above, in another example, the pusher includes first and second tabs extending radially from a body of the pusher.

Alternatively or additionally to any of the examples above, in another example, the first and second tabs of the pusher are positioned in first and second slots in the hub body, respectively.

Alternatively or additionally to any of the examples above, in another example, an internal rim of the lock nut engages the first and second tabs.

Alternatively or additionally to any of the examples above, in another example, the main port further includes a holder including first and second tabs extending radially from a body of the holder. The first and second tabs of the holder are positioned in the first and second slots in the hub body, respectively.

Alternatively or additionally to any of the examples above, in another example, the first tab of the pusher is positioned between an end surface of the first slot and the first tab of the holder, the second tab of the pusher is positioned between an end surface of the second slot and the second tab of the holder, and the first and second tabs of the pusher are axially movable in the first and second slots, respectively.

Another example is an introducer sheath. The introducer sheath includes a valve hub defining a main port and a side port, and an elongate shaft extending from the valve hub. The main port includes a hub body, a compressible seal disposed within the hub body, a pusher having a distal surface juxtaposed with a proximal surface of the compressible seal, and a holder coupled to the valve hub. A distal end region of the pusher extends into the hub body and is slidably movable relative thereto. A proximal end region of the pusher extends into the holder and is slidably movable relative thereto.

Alternatively or additionally to any of the examples above, in another example, the introducer sheath includes a lock nut surrounding the pusher. The lock nut is threadably engaged with the hub body such that rotation of the lock nut moves the pusher axially toward and/or away from the compressible seal.

Alternatively or additionally to any of the examples above, in another example, the main port includes a first O-ring surrounding the distal end region of the pusher and a second O-ring surrounding the proximal end region of the pusher.

Alternatively or additionally to any of the examples above, in another example, the pusher includes first and second tabs extending radially from a body of the pusher. The first and second tabs of the pusher are positioned in first and second slots in the hub body, respectively. The first and second tabs of the pusher are axially movable in the first and second slots, respectively.

Alternatively or additionally to any of the examples above, in another example, the holder includes first and second tabs extending radially from a body of the holder, wherein the first and second tabs of the holder are positioned in the first and second slots in the hub body, respectively.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
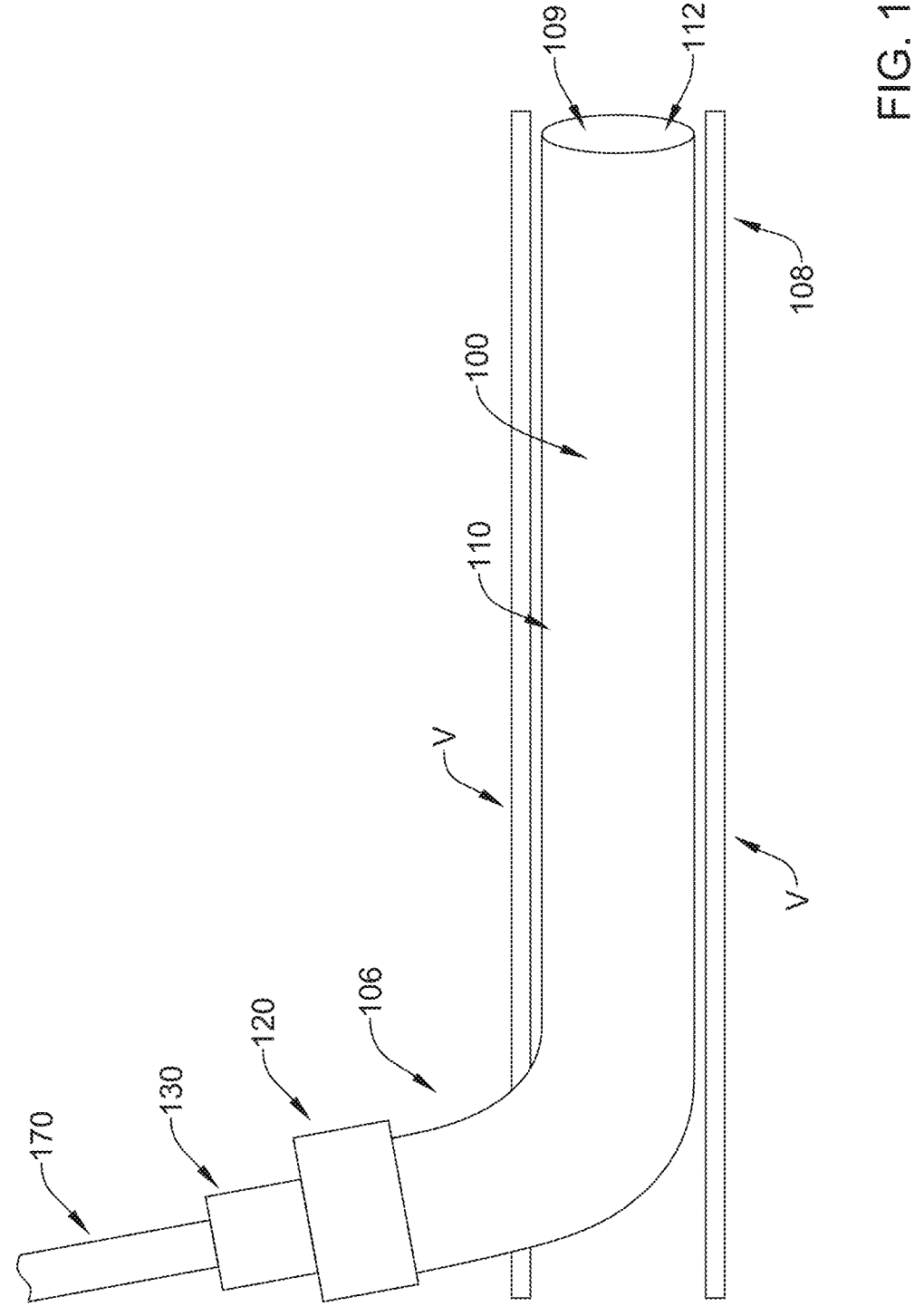
FIG. 1 is a side view of an introducer sheath extending into a blood vessel.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure. Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

Hemostasis valve hub assemblies provided with an introducer sheath facilitate insertion and positioning of one or more medical devices (e.g., catheters, blood pumps, guidewires, etc.) through the introducer sheath while also helping to prevent blood from leaking during a medical procedure. Some embodiments of the present disclosure feature assemblies with components that assist with fixing the position of one or more medical devices while maintaining a seal around the elongate shaft of the medical device to reduce blood loss through the hub assembly. Further, some embodiments may also provide components that facilitate convenient repositioning of the one or more medical devices relative to the introducer sheath.

FIG. 1 illustrates a side view of an introducer sheath 100 inserted at least partially into a blood vessel V, shown in cross-section. While the disclosure herein is made with reference largely to the introducer sheath 100, and components thereof, the disclosure may also apply to a repositioning sheath, as will be discussed further herein. In some embodiments, the introducer sheath 100 may be used for facilitating the passage of various medical devices, such as a catheter or a blood pump as will be described further herein, through the introducer sheath 100 and into the blood vessel V. Hence, in some instances the introducer sheath 100 may be referred to as a large bore introducer sheath. The introducer sheath 100 includes a proximal end region 106 proximate a proximal end of the introducer sheath 100 and a distal end region 108 proximate a distal end of the introducer sheath 100 that is opposite the proximal end region 106. A body portion 110 of the introducer sheath 100 extends between the proximal end region 106 and the distal end region 108, and the body portion 110 defines a lumen 112 of the introducer sheath 100. The introducer sheath 100 includes a proximal opening (not shown) adjacent the proximal end region 106 and a distal opening 109 adjacent the distal end region 108, with the lumen 112 extending from the proximal opening to the distal opening 109. The introducer sheath 100, or components thereof, may be formed by various materials, such as polymeric and/or metallic materials. In some instances, the introducer sheath 100, such as the elongate shaft of the introducer sheath 100, may include an additional surface coating, such as but not limited to, silicone, PET, or other applicable polymer.

A hemostasis valve hub 120 (hereinafter "hub 120" for brevity) may be provided at the proximal end region 106 to provide access to the lumen 112 of the introducer sheath 100. The hub 120 may be configured for hemostasis by, for example, helping to prevent blood from leaking out of the introducer sheath 100 during use. For example, a medical device 170, such as a catheter or blood pump, may be inserted through the hub 120 and lumen 112 of the introducer sheath 100 and into the blood vessel V, and the hub 120 may maintain hemostasis between the medical device 170, the introducer sheath 100, and the external surroundings. In some embodiments, the medical device 170, may include and/or be coupled to a blood pump 150, shown in FIG. 2. After insertion of the medical device, fixation of the axial and radial position of the medical device 170 may be desired to ensure that the medical device 170 (and any device coupled thereto) is maintained in a proper position during use. It may also be desired for the medical personnel to reposition the medical device 170 after insertion. As such, the hub 120 may include a tightening port 130, provided with or attachable thereto, that provides for the fixation of the medical device 170 with respect to the hub 120 and blood vessel V, as will be described further herein. The hub 120 and tightening port 130 may allow for the repositioning of the medical device 170 with respect to the hub 120 and the blood vessel V.

Figure 2:
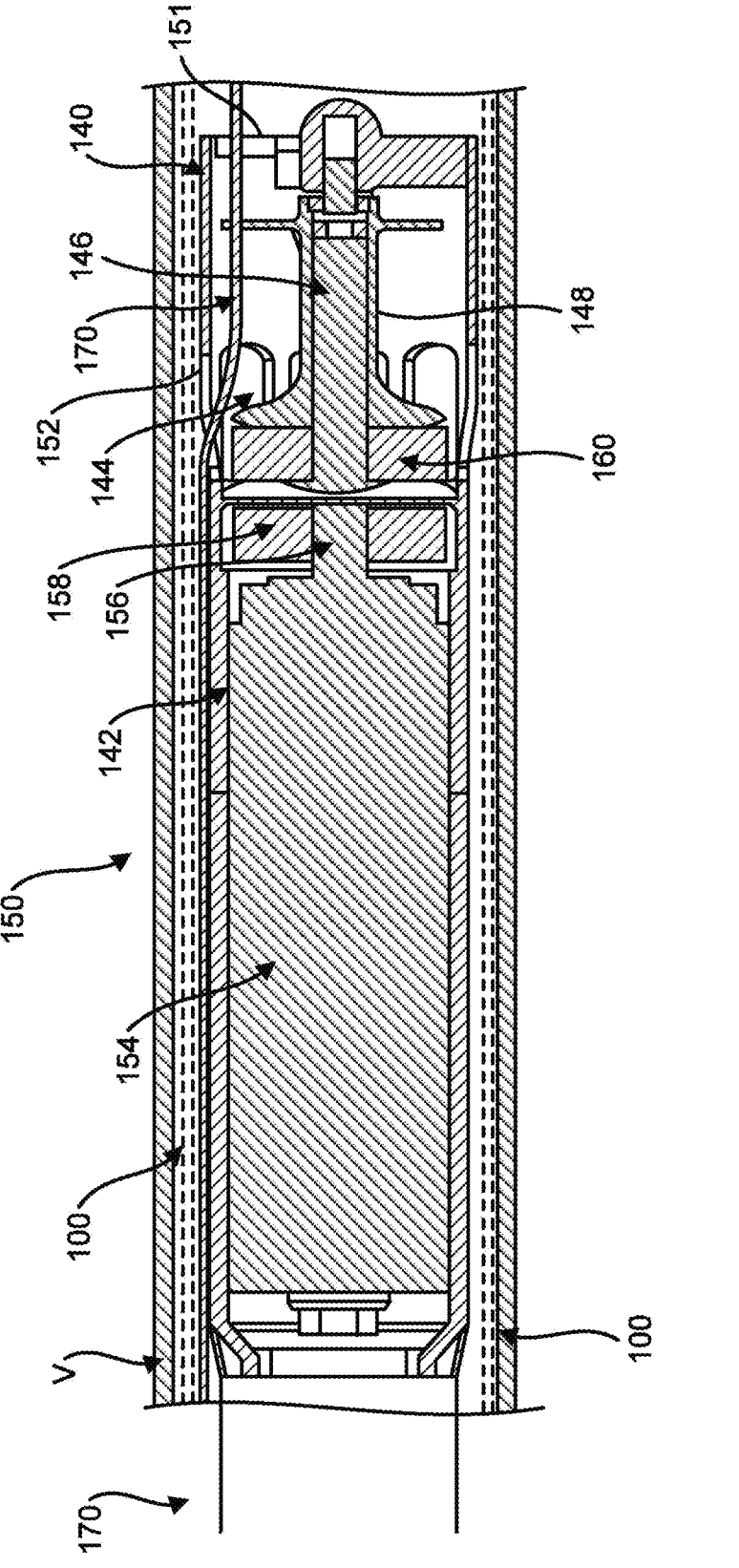
FIG. 2 is a cross-sectional view of a portion of the introducer sheath of FIG. 1 inserted into a blood vessel, and a medical device inserted into the introducer sheath.

FIG. 2 illustrates a cross-sectional view of the body portion 110 of the introducer sheath 100 of FIG. 1 upon insertion of a medical device, illustratively a blood pump 150, into the introducer sheath 100. As noted above, the medical device 170 of FIG. 1 may be coupled to or include the blood pump 150, with the medical device 170 extending outside the blood vessel V and the introducer sheath 100. The blood pump 150 may be advanced through the blood vessel V and positioned in a target location, such as a target cardiac location (e.g., the left ventricle), via the introducer sheath 100. The blood pump 150 may generally include an impeller assembly housing 140 and a motor housing 142. In some embodiments, the impeller assembly housing 140 and the motor housing 142 may be integrally or monolithically constructed. In other instances, the impeller assembly housing 140 and the motor housing 142 may be separate components. The impeller assembly housing 140 carries an impeller assembly 144 therein. The impeller assembly 144 may include an impeller shaft 146 and an impeller 148 that rotate relative to the impeller assembly housing 140 to drive blood through the blood pump 150. More specifically, the rotation of the impeller 148 causes blood to flow from a blood inlet 151 formed on the impeller assembly housing 140, through the impeller assembly housing 140, and out of a blood outlet 152 formed on the impeller assembly housing 140. In some embodiments, the impeller shaft 146 and the impeller 148 may be integrally formed, whereas, in other embodiments the impeller shaft 146 and the impeller 148 may be separate components. As shown in FIG. 2, the inlet 151 may be formed on an end portion of the impeller assembly housing 140 and the outlet 152 may be formed on a side portion of the impeller assembly housing 140. In other embodiments, the inlet 151 and/or the outlet 152 may be formed on other portions of the impeller assembly housing 140. In some embodiments, the impeller assembly housing 140 may be coupled to a distally extending cannula, and the cannula may receive and deliver blood to the inlet 151.

With continued reference to FIG. 2, the motor housing 142 carries a motor 154, and the motor 154 is configured to rotatably drive the impeller 148 relative to the impeller assembly housing 140. In the illustrated embodiment, the motor 154 rotates a drive shaft 156, which is coupled to a driving magnet 158. Rotation of the driving magnet 158 causes rotation of a driven magnet 160, which is connected to the impeller assembly 144. More specifically, in embodiments incorporating the impeller shaft 146, the impeller shaft 146 and the impeller 148 are configured to rotate with the driven magnet 160. In other embodiments, the motor 154 may be coupled to the impeller assembly 144 via other components. While the introducer sheath 100 is illustrated above with the use of the blood pump 150, various other medical devices may be used in conjunction with the introducer sheath 100 and the hemostasis valve hub 120.

Figure 3:
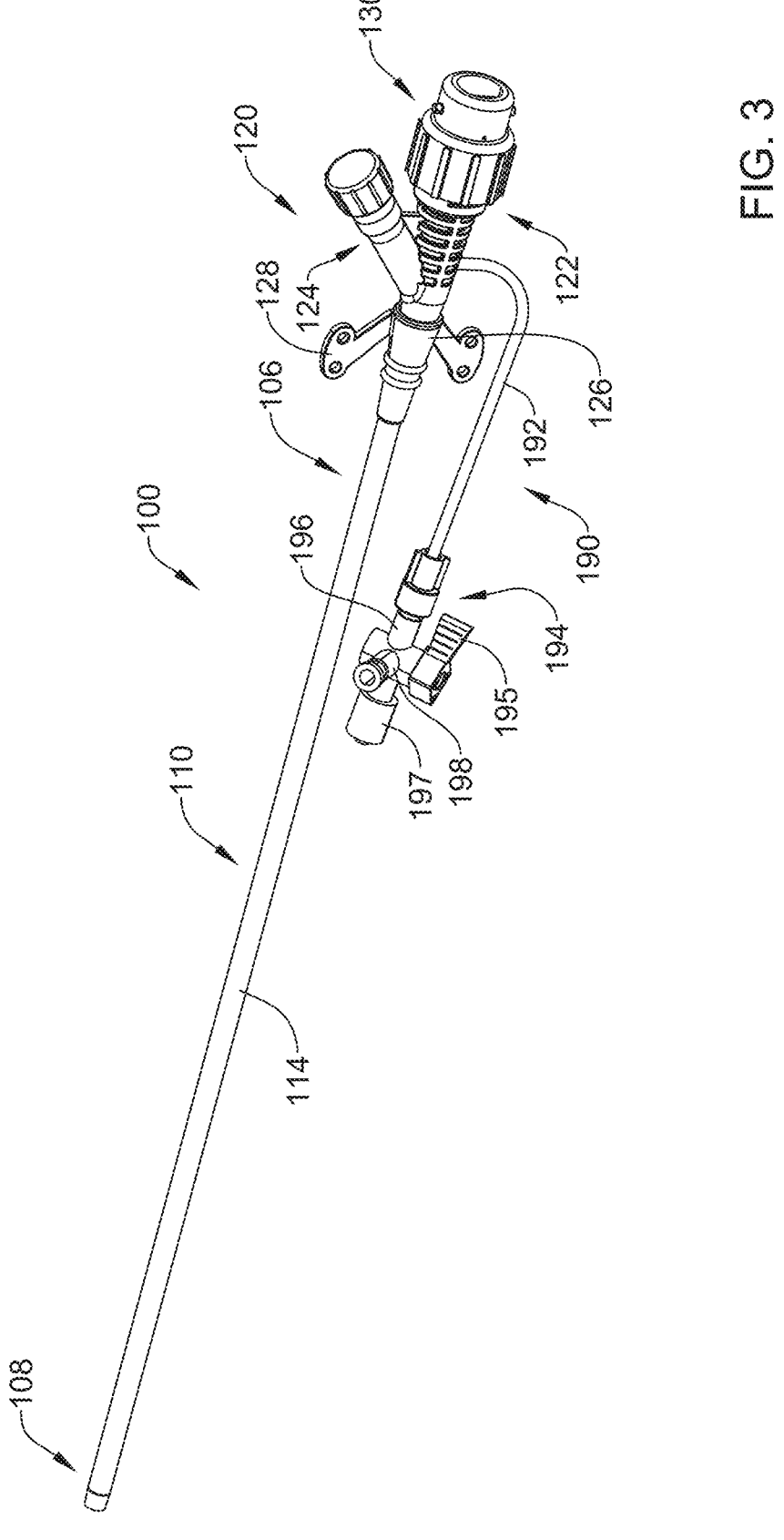
FIG. 3 is a perspective view of the introducer sheath of FIG. 1.

FIG. 3 is a perspective view of the introducer sheath 100 of FIG. 1 in which further details of the introducer sheath 100 are illustrated. For example, the introducer sheath 100 includes the hub 120, an elongate shaft 114 extending distally from the hub and defining the body portion 110 of the sheath 100. The sheath 100 may also include a flush line 190 extending from the hub 120. The flush line 190 may include a tubular member 192 extending from the hub 120 and in fluid communication with a lumen of the hub 120. The tubular member 192 may extend to a stopcock 194, such as a three-way stopcock. The stopcock 194 may include a first leg 196 coupled to the tubular member 192, a second leg 197, a third leg 198, and a lever 195 that is rotatable to selectively open/close fluid access between the first, second and/or third legs 196, 197, 198. Each of the legs 196, 197, 198 may include a connector, such as a luer connector, as desired.

The hub 120 may also include a strain relief 126 configured to provide a transition flexibility along the proximal end region 106. The strain relief 126 may include a body attached to a main body of the hub 120, as will be described further herein. The strain relief 126 may include one or more suture pads 128 extending outward therefrom. For example the strain relief 126 may include first and second suture pads 128 extending from opposite sides of the strain relief 126. The suture pads 128 may facilitate securing the hub 120 against the patient once the introducer sheath 100 has been positioned in the blood vessel of the patient. For example, each suture pad 128 may include at least one opening extending therethrough for receiving a suture used to suture the hub 120 to the skin of the patient.

The suture pads 128 may be angled at an acute angle relative to the longitudinal axis of the sheath 100. For instance, the suture pads 128 may be angled toward the distal end region 108 of the sheath 100 such that the free ends of the suture pads 128 are positioned distal of the base ends of the suture pads 128. In some instances, the angle between the suture pads 128 and the longitudinal axis of the sheath 100 may be about 30 degrees to about 90 degrees, about 35 degrees to about 85 degrees, about 40 degrees to about 80 degrees, about 45 degrees to about 75 degrees, about 50 degree to about 70 degrees, or about 55 degrees to about 65 degrees. In some instances the angle between the suture pads 128 and the longitudinal axis of the sheath 100 may be about 35 degrees, 40 degrees, 45 degrees, 50 degrees, 55 degrees, or 60 degrees.

Figure 6:
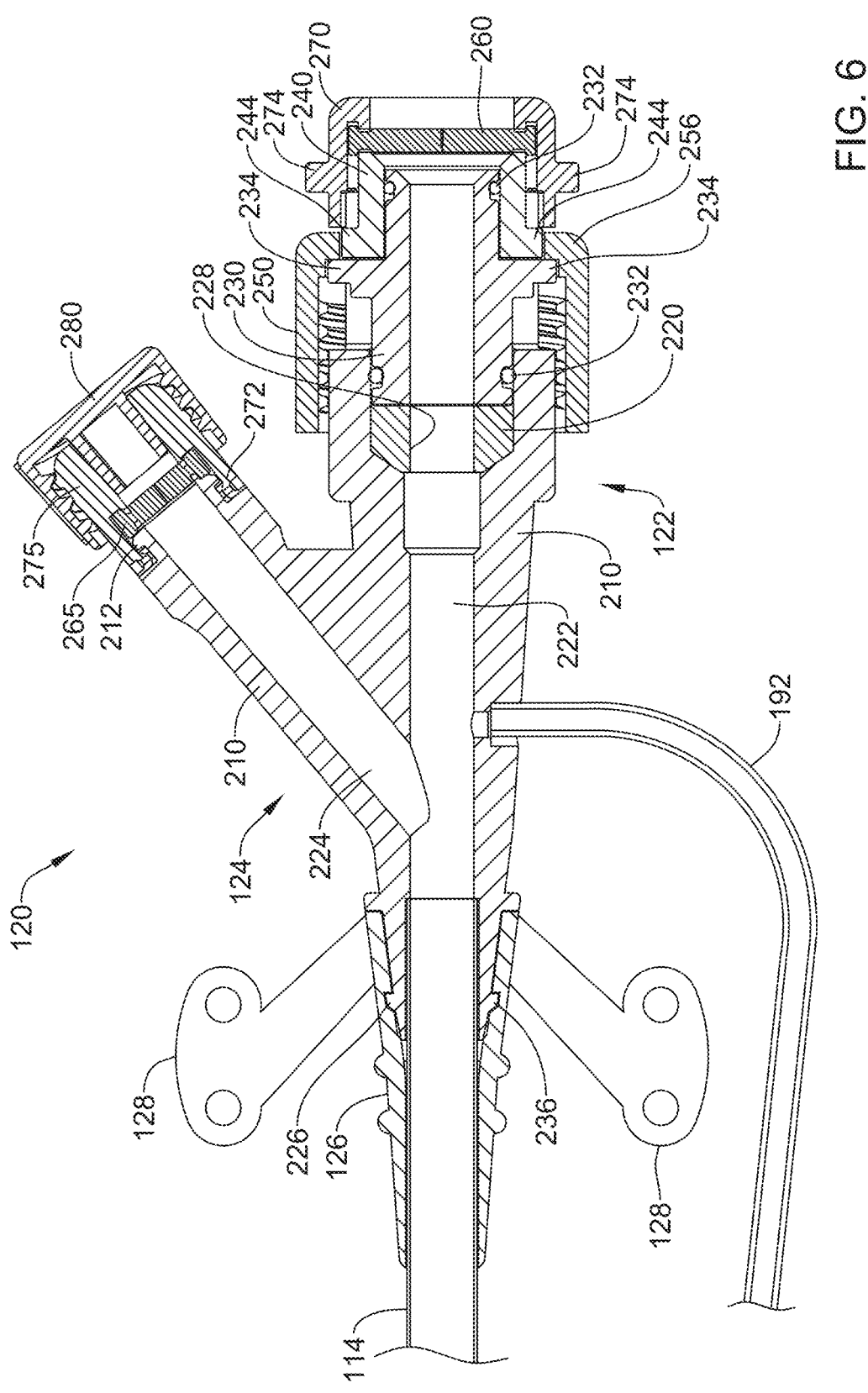
FIG. 6 is a cross-sectional view of a portion of the introducer sheath of FIG. 3.

As further shown in FIG. 6, a distal end portion of the hub body 210 may extend into the interior of the strain relief 126 and be coupled thereto. For example, the hub body 210 may include an annular rim 226 configured to engage (e.g., form a snap fit) with a mating recess 236 formed in the interior of the strain relief 126.

The hub 120 may include a main port 122 and a side port 124 extending from the main port 122. In some instances the side port 124 may extend at an acute angle or a perpendicular angle from the main port 122. The main port 122 and/or the side port 124 may provide access to one or more lumens extending through the body portion 110 of the sheath 100. In some instances, the main port 120 may be the tightening port 130, as discussed above.

Figure 4:
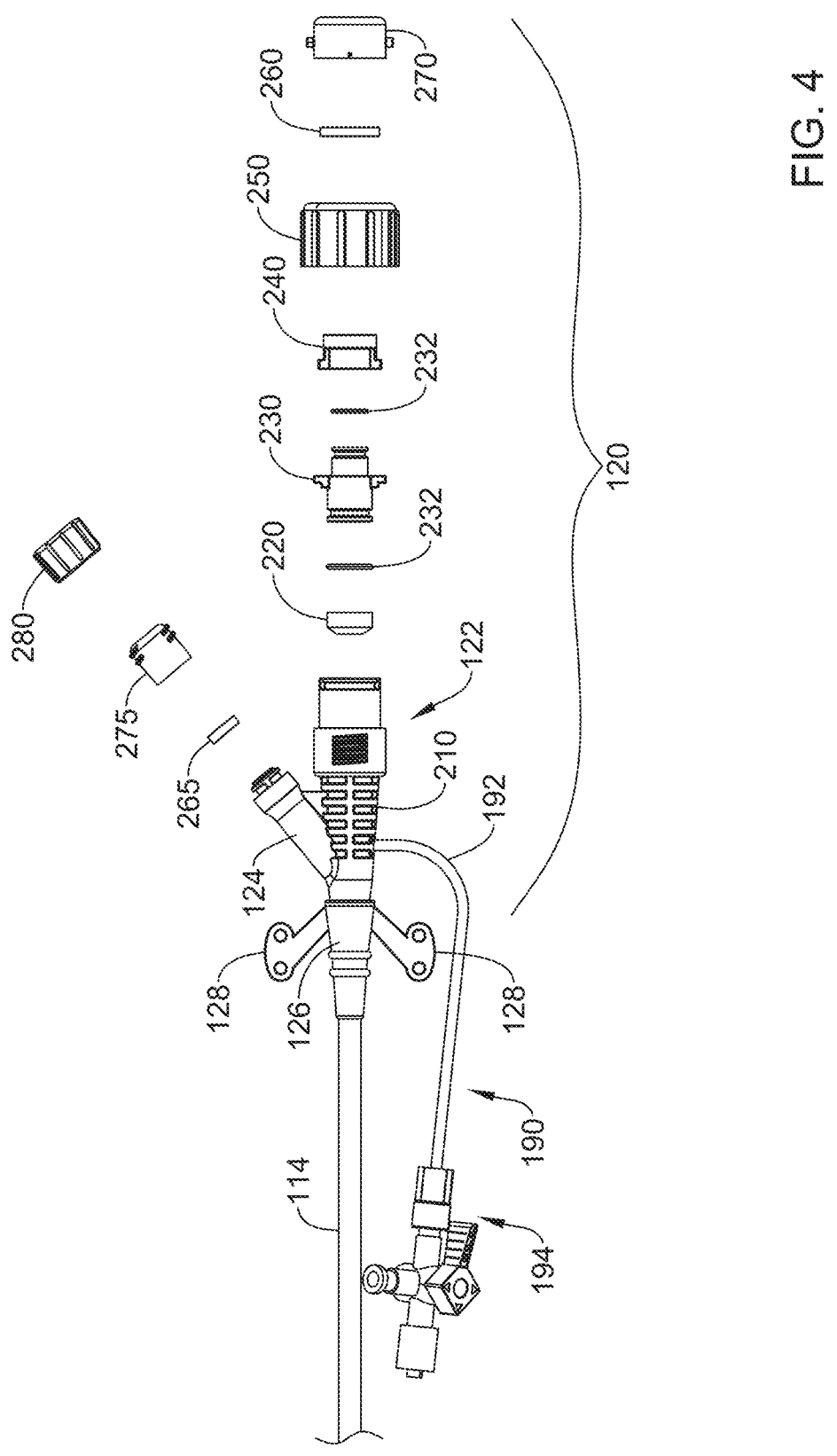
FIG. 4 is an exploded side view of various components of the introducer sheath of FIG. 3.
Figure 5:
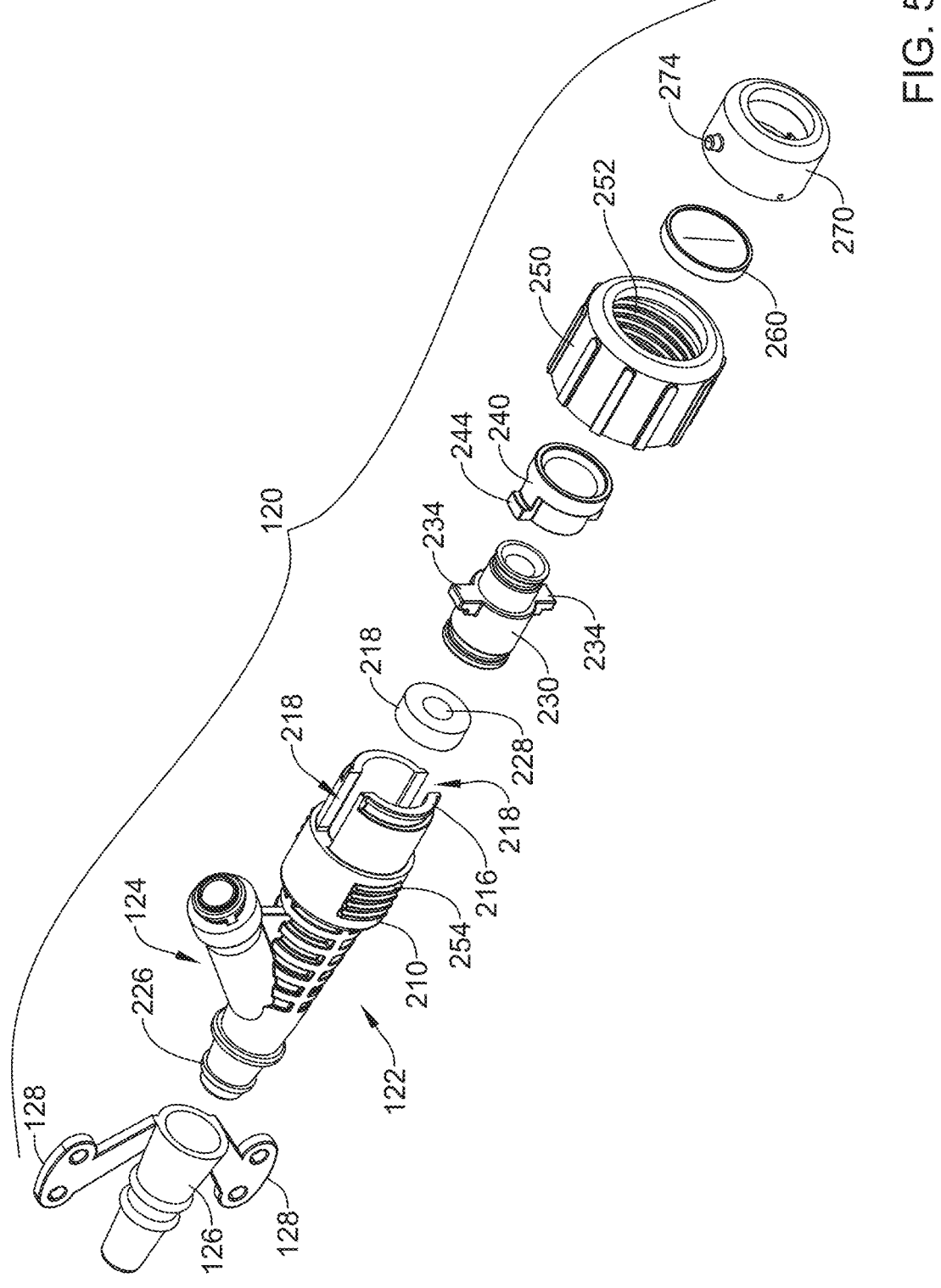
FIG. 5 is an exploded perspective view of various components of the introducer sheath of FIG. 3.

Further details of the components of the hub 120 are shown in the exploded side view of FIG. 4 and the exploded perspective view of FIG. 5, and the cross-sectional view of FIG. 6. The main port 122 of hub 120 may include a hub body 210. In some instances, the hub body 210 may be a molded, one-piece structure. For example, the hub body 210 may be molded from a polymeric material. In other instances, the hub body 210 may be formed of two or more components attached together. In some instances the hub body 210 may also include or be connected to the hub body of the side port 124.

The side port 124 may include a passage 224 extending therethrough and an elastomeric seal 265 positioned along the passage 224 of the side port 124. For example, hub body 210 may define the passage 224. The elastomeric seal 265 may be a slit valve (e.g., a cross-slit valve), a dome valve, a duckbill valve, or any other desired valve configured to seal around an elongate shaft of a medical device when passed therethrough. In some instances, the elastomeric seal 265 may include one or more slits (e.g., crossing slits) extending entirely through the seal wall and/or one or more slits (e.g., crossing slits) extending only partially through the seal wall. For instance, the elastomeric seal 265 may be a cross-slit valve having a first slit extending into the wall of the seal from a first side of the seal but not extend entirely through the wall of the seal and a second slit extending into the wall of the seal from a second, opposite side of the seal but not extend entirely through the wall of the seal. The first slit may intersect the second slit within the wall of the valve. In some instances, the first slit may be arranged perpendicular to the second slit. The elastomeric seal 265 may be formed of any desired flexible material, such as silicone, polyurethane, etc.

The side port 124 may also include a side port lid 275 connectable to the hub body 210. For example, the side port lid 275 may include a lip 272, shown in FIG. 6, configured to engage (e.g., form a snap fit) with a mating rim 212 of the hub body 210. In some instances, the side port lid 275 may include an anti-rotation feature, such as a tab or a groove, configured to mate with a corresponding anti-rotation feature, such as a groove or a tab, of the hub body 210. The elastomeric seal 265 may be housed in the side port lid 275 such that the elastomeric seal 265 is captured between an upper surface of the hub body 210 and an internal surface of the side port lid 275.

The side port 124 may also include a side port cap 280 configured to threadably engage the side port lid 275. For example, the side port cap 280 may include internal threads configured to threadably engage external threads in the side port lid 275. Removal of the side port cap 280 may allow access to the elastomeric seal 265 such that a medical device may be passed through the elastomeric seal 265 into the side port passageway 224.

The main port 122, may include a passage 222 extending therethrough. For example, the hub body 210 may define the passage 222. The passage 224 of the side port 124 may converge with the passage 222 of the main port 122 within the hub body 210. The passage 222 and/or the passage 224 may be in fluid communication with the lumen 112 of the sheath 100 extending to the distal opening 109 (See FIG. 1).

The main port 122 may include a primary seal and a secondary seal spaced apart from the primary seal along a length of the main port 122. For example, the main port 122 may include a compressible seal (e.g., Tuohy seal) 220 and an elastomeric seal 260 spaced apart from the compressible seal 220. The main port 122, which may be considered a tightening port, may further include a pusher 230, a holder 240, a lock nut 250, and/or a main port lid 270. Rotation of the lock nut 250 may actuate the pusher 230 toward/away from the compressible seal 220 to adjust the size of the opening 228 through the compressible seal 220. As described further herein, the compressible seal 220 may be movable between an open state, allowing a medical device to pass through the opening 228, and a closed state, sealing the compressible seal 220 around the medical device. The compressible seal 220 may be formed of any desired flexible material, such as silicone, polyurethane, etc.

As shown in FIG. 6, the compressible seal 220 may be positioned in the interior of the hub body 210 with the opening 228 of the compressible seal 220 axially aligned with the passageway 222 of the main port 122. A distal end region of the pusher 230 may be positioned in the interior of the hub body 210 with a distal end surface of the pusher 230 juxtaposed with a proximal end surface of the compressible seal 220. A lumen extending through the pusher 230 may be axially aligned with the compressible seal 220 and/or the passageway 222. The pusher 230 may include one or more tabs 234 extending outward therefrom configured to be positioned in one or more slots 218 formed in the hub body 210. For example, the pusher 230 may include first and second tabs 234 extending from opposite sides of the pusher 230. The first and second tabs 234 may be positioned in first and second slots 218, respectively, formed in the hub body 210. Positioning the tabs 234 in the slots 218 may prevent rotational movement of the pusher 230 relative to the hub body 210 and/or the compressible seal 220 while permitting axial movement of the pusher 230 relative to the hub body 210 to move the pusher 230 toward and/or away from the compressible seal 220. The tabs 234 may be located on an intermediate region of the pusher such that a distal end region of the pusher 230 may extend distal of the tabs 234 and a proximal end region of the pusher 230 may extend proximal of the tabs 234.

The holder 240 may include first and second tabs 244 extending outward therefrom configured to be positioned in the first and second slots 218, respectively, formed in the hub body 210 while a rim of the holder 240 is juxtaposed with the proximal end face of the hub body 210. The tabs 234 of the pusher 230 may be captured between a distal edge of the slots 218 and the tabs 244 of the holder 240, allowing the tabs 234 of the pusher 230 a range of axial travel between a distalmost position proximate the distal edge of the slots 218 and a proximalmost position proximate the tabs 244 of the holder 240. A proximal end region of the pusher 230 may extend into the interior of the holder 240.

The main port lid 270 may be connectable to the hub body 210 with the holder 230 therebetween, thereby securing the holder 230 relative to the hub body 210. For example, the main port lid 270 may include a lip configured to engage (e.g., form a snap fit) with a mating rim 216 of the hub body 210. In some instances, the main port lid 270 may include an anti-rotation feature, such as an engagement surface, con-figured to mate with a corresponding anti-rotation feature, such as an engagement surface, of the hub body 210. In addition or alternative to forming a snap fit, the main port lid 270 may be adhesively bonded to the hub body 210, or otherwise secured to the hub body 210.

The main port lid 270 may include a coupling interface (e.g., one or more couplers) configured such that a sterile sleeve may be coupled to the hub 120. For example, a sterile sleeve (not shown), which may be placed around (e.g., surround) the elongate shaft of the medical device, may be coupled to the hub 120 to maintain a sterile field during a medical procedure and/or while using the medical device 170. For instance, the main port lid 270 may include one or more, or a plurality of locking features 274, such as pins shown in FIG. 5, for coupling a sterile sleeve to the hub 120. The main port lid 270 may include locking features 274 (e.g., first and second pins) extending in opposite directions from opposing sides of the main port lid 270. In other instances, the locking features 274 (e.g., first and second pins) may be used to connect a dilator cap to the hub 120 in a similar manner.

The elastomeric seal 260 may be housed in the main port lid 270 such that the elastomeric seal 260 is captured between an end surface of the holder 240 and an internal surface of the main port lid 270. The main port lid 270 may extend distally beyond the elastomeric seal 260 such that a distal end region of the main port lid 270 surrounds the holder 240. The elastomeric seal 260 may be a slit valve (e.g., a cross-slit valve), a dome valve, a duckbill valve, or any other desired valve configured to seal around an elon-gate shaft of a medical device when passed therethrough. In some instances, the elastomeric seal 260 may include one or more slits (e.g., crossing slits) extending entirely through the seal wall and/or one or more slits (e.g., crossing slits) extending only partially through the seal wall. For instance, the elastomeric seal 260 may be a cross-slit valve having a first slit extending into the wall of the seal from a first side of the seal but not extend entirely through the wall of the seal and a second slit extending into the wall of the seal from a second, opposite side of the seal but not extend entirely through the wall of the seal. The first slit may intersect the second slit within the wall of the valve. In some instances, the first slit may be arranged perpendicular to the second slit. The elastomeric seal 260 may be formed of any desired flexible material, such as silicone, polyurethane, etc. The pusher 230 may be positioned entirely between the com-pressible seal 220 and the elastomeric seal 260.

The lock nut 250 may be assembled such that the lock nut 250 surrounds a proximal portion of the hub body 210. The lock nut 250 may include internal threading 252 threadably engaged with external threading 254 provided on an exterior of the proximal portion of the hub body 210.

As shown in the cross-sectional view of FIG. 6, the components of the main port 122 may form a hemostasis valve. Accordingly, rotating the lock nut 250 in a first rotational direction causes the lock nut 250 to travel distally relative to the hub body 210, and rotating the lock nut 250 in a second, opposite rotational direction causes the lock nut 250 to travel proximally relative to the hub body 210. As shown in FIG. 6, the lock nut 250 may include an internal rim 256 configured to engage the first and second tabs 234 of the pusher 230. For example, a distal facing surface of the internal rim 256 may engage a proximally facing surface of the first and second tabs 234 of the pusher 230. The internal rim 256 may extend continuously around the lock nut 250. Thus the distally facing surface of the internal rim 256 may maintain engagement with the first and second tabs 234 as the lock nut 250 is rotated through one or more full revo-lutions. As the lock nut 250 is rotated, and thus travels axially along the hub body 210, the lock nut drives the pusher 230 in an axial direction. For example, as the lock nut 250 is rotated in a first rotational direction relative to the hub body 210, the lock nut 250 travels distally, urging the pusher 230 to travel distally relative to the hub body 210 to exert a compressive force on the compressible seal 220 to thereby reduce the diameter of the opening 228 through the com-pressible seal 220. As the lock nut 250 is rotated in a second rotational direction relative to the hub body 210, the lock nut 250 travels proximally, permitting the pusher 230 to travel proximally relative to the hub body 210 to reduce and/or remove the compressive force on the compressible seal 220 to thereby increase the diameter of the opening 228 through the compressible seal 220.

The main port 122 may include a first O-ring 232 sur-rounding the distal end region of the pusher 230, forming a seal between the distal end region of the pusher 230 and an internal surface of the hub body 210. Furthermore, the main port 122 may include a second O-ring 232 surrounding the proximal end region of the pusher 230, forming a seal between the proximal end region of the pusher 230 and an internal surface of the holder 240. The first O-ring 232 may have a diameter which is the same or different from a diameter of the second O-ring 232. For example, as shown in FIG. 4, the diameter of the first O-ring (the distal O-ring) may be greater than the diameter of the second O-ring (the proximal O-ring). In other instances, the diameter of the first O-ring (the distal O-ring) may be less than the diameter of the second O-ring (the proximal O-ring). The O-rings 232 prevent blood from escaping through the interface between the distal end region of the pusher 230 and the hub body 210 and/or escaping through the interface between the proximal end region of the pusher 230 and the holder 240 while permitting the pusher 230 to move axially relative to the hub body 210 and the holder 240.

In other embodiments, the position of the elastomeric seal 260 and the compression seal 220 may be revised, with the elastomeric seal 260 located distal of the compression seal 220. In some such embodiments, the pusher 230 may be positioned entirely between the compressible seal 220 and the elastomeric seal 260. In such an instance, as the lock nut 250 is rotated in a first rotational direction relative to the hub body 210, the lock nut 250 may travel proximally, urging the pusher 230 to travel proximally relative to the hub body 210 to exert a compressive force on the compressible seal 220

(located proximal of the pusher 230) to thereby reduce the diameter of the opening 228 through the compressible seal 220. As the lock nut 250 is rotated in a second rotational direction relative to the hub body 210, the lock nut 250 travels distally, permitting the pusher 230 to travel distally relative to the hub body 210 to reduce and/or remove the compressive force on the compressible seal 220 to thereby increase the diameter of the opening 228 through the compressible seal 220. Other arrangements are contemplated for positioning the pusher 230 relative to the compressible seal 220 to apply a compressive force thereto.

Figure 7:
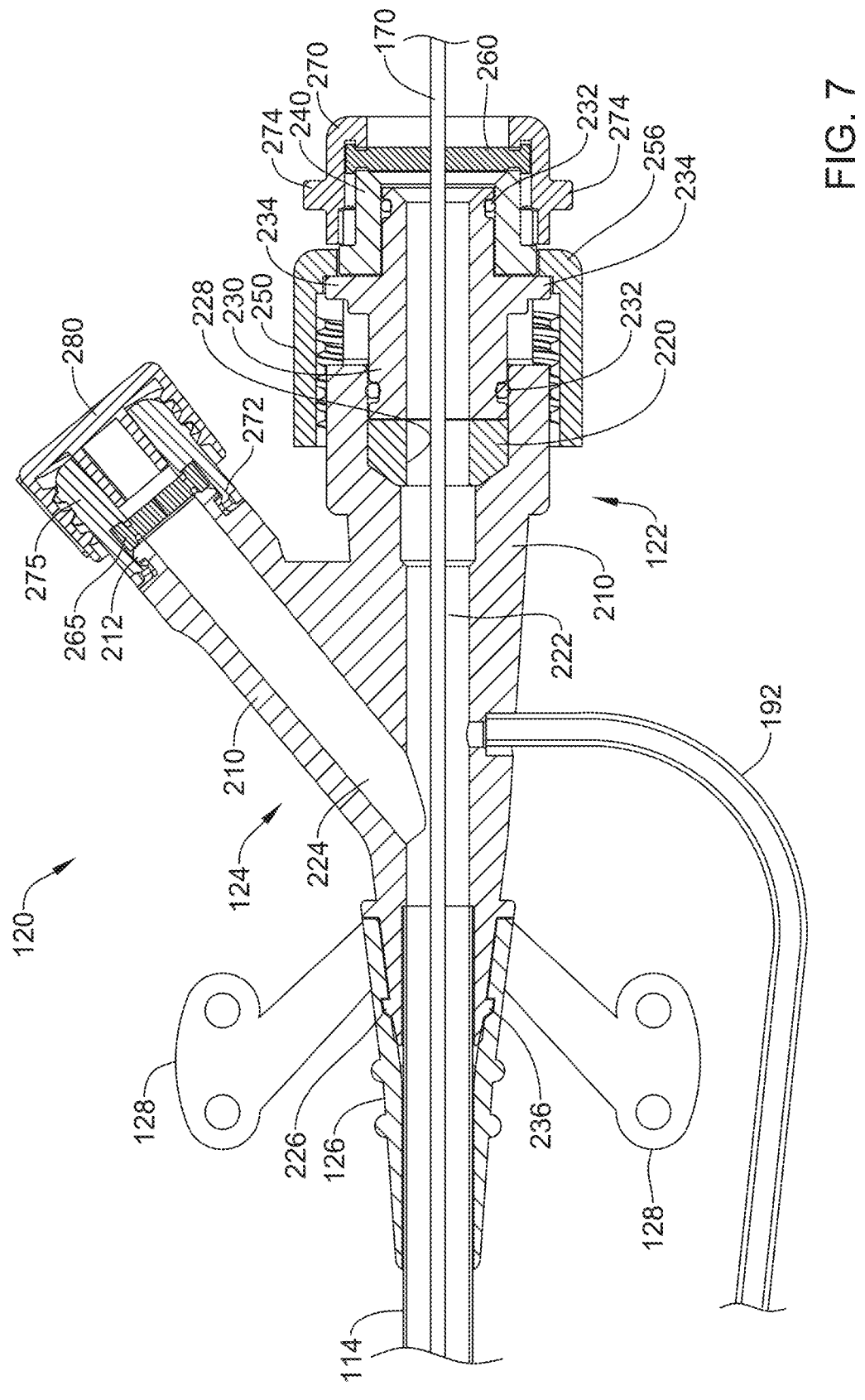
FIG. 7 is a cross-sectional view of the introducer sheath of FIG. 3 with a medical device passing through the hemostasis valve in an open position.
Figure 8:
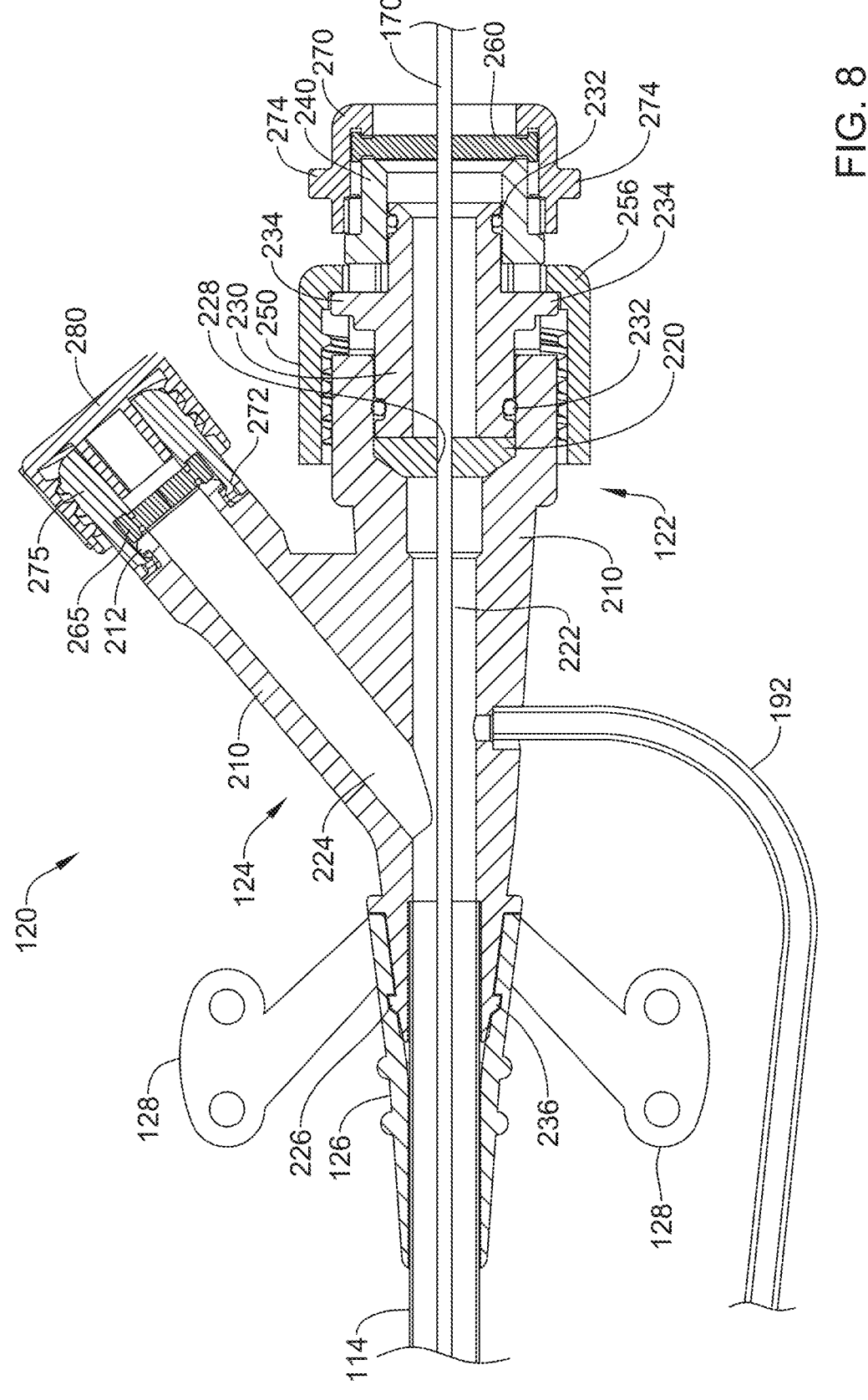
FIG. 8 is a cross-sectional view of the introducer sheath of FIG. 3 with a medical device passing through the hemostasis valve in a closed position.

FIG. 7 is a cross-sectional view of the introducer sheath 100 of FIG. 3 with a medical device 170 passing through the hemostasis valve in an open position. FIG. 8 is a cross-sectional view of the introducer sheath of FIG. 3 with a medical device passing through the hemostasis valve in a closed position. In some instances, the main port 122 (e.g., hemostasis port) may be configured to accommodate a medical device having a diameter of 12 F or more, 14 F or more, 15 F or more, 16 F or more, or 17 F or more. In other words, the compressible seal 220 and the elastomeric seal 260 may be configured to permit a medical device having a diameter of 12 F or more, 14 F or more, 15 F or more, 16 For more, or 17 F or more, to pass therethrough while maintaining hemostasis.

In use, an elongate shaft of a medical device 170 may be inserted through the elastomeric seal 260, through the lumen of the pusher 230, through the opening 228 of the compressible seal 220 and into the passageway 222 of the main port 122. For example, the elongate shaft of the medical device 170 may be passed through an opening of the elastomeric seal 260 and cause the elastomeric seal 260 to flex and/or deform to permit the elongate shaft of the medical device 170 to be advanced therethrough. The elastomeric seal 260 may seal around an outer perimeter of the elongate shaft of the medical device 170 and substantially prevent blood from escaping from the main port 122. Thereafter, the elongate shaft of the medical device 170 passes through the opening 228 of the compressible seal 220 into the passageway 220 of the main port 122. The elongate shaft of the medical device 170 may be further advanced through the elongate shaft 114 of the sheath 100 into the body of the patient for a diagnostic and/or therapeutic procedure. As shown in FIG. 8, once the elongate shaft of the medical device 170 is positioned at a desired location within the vasculature of the patient, the compressible seal 220 may be compressed or tightened around the perimeter of the elongate shaft of the medical device 170 to prevent blood from leaking past the medical device 170 and out of the main port 122 and/or lock the elongate shaft of the medical device 170 from axial movement relative to the hub 120. For instance, as discussed above, the lock nut 250 may be rotated to distally advance the pusher 230, which in turn exerts a compressive force against the compressible seal 220, reducing the diameter of the opening 228 through the compressible seal 220, to seal the compressible seal 220 around the elongate shaft of the medical device 170.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An introducer sheath, comprising:
a valve hub defining a main port and a side port; and
an elongate shaft extending from the valve hub;
wherein the main port includes:
   a hub body;
   a compressible seal disposed within the hub body;
   a pusher at least partially positioned within the hub body and slidably movable relative thereto; and
   a lock nut surrounding the pusher, the lock nut threadably engaged with the hub body such that rotation of the lock nut moves the pusher axially toward and/or away from the compressible seal;
   wherein the pusher includes first and second tabs extending radially from a body of the pusher, the first and second tabs of the pusher are positioned in first and second slots in the hub body, respectively; and
   a holder including first and second tabs extending radially from a body of the holder, wherein the first and second tabs of the holder are positioned in the first and second slots in the hub body, respectively.

2. The introducer sheath of claim 1, wherein the first and second tabs of the pusher extend in opposite directions.

3. The introducer sheath of claim 1, wherein an internal rim of the lock nut engages the first and second tabs of the pusher.

4. The introducer sheath of claim 1, further comprising a first O-ring surrounding a distal portion of the pusher and a second O-ring surrounding a proximal portion of the pusher.

5. The introducer sheath of claim 4, wherein the first and second tabs are located between the first O-ring and the second O-ring.

6. The introducer sheath of claim 1, wherein the pusher extends proximal of the hub body.

7. The introducer sheath of claim 1, wherein the main port includes an elastomeric seal, wherein the pusher is positioned between the compressible seal and the elastomeric seal.

8. The introducer sheath of claim 1, wherein the side port includes an elastomeric seal including one or more slits formed therein.

9. An introducer sheath, comprising:
a valve hub defining a main port and a side port; and
an elongate shaft extending from the valve hub;
wherein the main port includes:
   a hub body:
   a compressible seal disposed within the hub body:
   an elastomeric seal proximal of and spaced apart from the compressible seal;
   a lock nut threadably engaged with the hub body such that rotation of the lock nut moves the compressible seal between an opening position and a closed position;
   a pusher engaged with the lock nut, such that rotation of the lock nut causes the pusher to axially move toward and/or away from the compressible seal;
   wherein the pusher includes first and second tabs extending radially from a body of the pusher, the first and second tabs of the pusher are positioned in first and second slots in the hub body, respectively;
   wherein an internal rim of the lock nut engages the first and second tabs; and
   a holder including first and second tabs extending radially from a body of the holder, wherein the first and second tabs of the holder are positioned in the first and second slots in the hub body, respectively.

10. The introducer sheath of claim 9, wherein:

the first tab of the pusher is positioned between an end surface of the first slot and the first tab of the holder;

the second tab of the pusher is positioned between an end surface of the second slot and the second tab of the holder; and the first and second tabs of the pusher are axially movable in the first and second slots, respectively.

11. An introducer sheath, comprising:

a valve hub defining a main port and a side port; and an elongate shaft extending from the valve hub;

wherein the main port includes:

a hub body;

a compressible seal disposed within the hub body;

a pusher having a distal surface juxtaposed with a proximal surface of the compressible seal; and a holder coupled to the valve hub;

wherein a distal end region of the pusher extends into the hub body and is slidably movable relative thereto; and wherein a proximal end region of the pusher extends into the holder and is slidably movable relative thereto;

wherein the pusher includes first and second tabs extending radially from a body of the pusher, the first and second tabs of the pusher are positioned in first and second slots in the hub body, respectively, and the first and second tabs of the pusher are axially movable in the first and second slots, respectively.

12. The introducer sheath of claim 11, further comprising a lock nut surrounding the pusher, the lock nut threadably engaged with the hub body such that rotation of the lock nut moves the pusher axially toward and/or away from the compressible seal.

13. The introducer sheath of claim 11, further comprising a first O-ring surrounding the distal end region of the pusher and a second O-ring surrounding the proximal end region of the pusher.

14. The introducer sheath of claim 11, wherein the holder includes first and second tabs extending radially from a body of the holder, wherein the first and second tabs of the holder are positioned in the first and second slots in the hub body, respectively.

\* \* \* \* \*